(12) United States Patent
Junqueira et al.

(10) Patent No.: US 11,478,516 B2
(45) Date of Patent: Oct. 25, 2022

(54) PROBIOTIC BACTERIA-DIRECTED PREVENTION OR TREATMENT OF FUNGAL INFECTION

(71) Applicants: Rhode Island Hospital, Providence, RI (US); Universidade Estadual Paulista/UNESP, São José Dos Campos (BR)

(72) Inventors: Juliana Campos Junqueira, São José Dos Campos (BR); Helen Burgwyn Fuchs, Quincy, MA (US); Eleftherios Mylonakis, Providence, RI (US)

(73) Assignees: RHODE ISLAND HOSPITAL, Providence, RI (US); UNIVERSIDADE ESTADUAL PAULISTA/UNESP, Sao Paulo (BR)

( * ) Notice: Subject to any disclaimer, the term of this patent is extended or adjusted under 35 U.S.C. 154(b) by 0 days.

(21) Appl. No.: 16/321,008

(22) PCT Filed: Jul. 31, 2017

(86) PCT No.: PCT/US2017/044703
§ 371 (c)(1),
(2) Date: Jan. 25, 2019

(87) PCT Pub. No.: WO2018/026719
PCT Pub. Date: Feb. 8, 2018

(65) Prior Publication Data
US 2019/0151382 A1    May 23, 2019

Related U.S. Application Data

(60) Provisional application No. 62/369,735, filed on Aug. 1, 2016.

(51) Int. Cl.
*A61K 35/747* (2015.01)
*A23L 33/135* (2016.01)
*A61P 31/10* (2006.01)
*A61P 3/00* (2006.01)
*C12N 1/20* (2006.01)
*A23L 29/00* (2016.01)
*C12R 1/225* (2006.01)

(52) U.S. Cl.
CPC .......... *A61K 35/747* (2013.01); *A23L 29/065* (2016.08); *A23L 33/135* (2016.08); *A61P 3/00* (2018.01); *A61P 31/10* (2018.01); *C12N 1/20* (2013.01); *C12N 1/205* (2021.05); *A23V 2002/00* (2013.01); *A23V 2200/3204* (2013.01); *A23Y 2220/63* (2013.01); *C12R 2001/225* (2021.05)

(58) Field of Classification Search
CPC ... A61K 35/747; A23L 29/065; A23L 33/135; A61P 3/00; A61P 31/10; C12N 1/205; C12N 1/20; C12R 2001/225; A23V 2002/00; A23V 2200/3204; A23V 2220/63
USPC ....................................................... 424/93.45
See application file for complete search history.

(56) References Cited

U.S. PATENT DOCUMENTS

| | | | |
|---|---|---|---|
| 2009/0117056 A1* | 5/2009 | Hodal, Jr. ............ | A61K 35/747 424/48 |
| 2014/0356337 A1* | 12/2014 | Lejeune ................. | A21D 8/047 424/93.44 |
| 2016/0101136 A1 | 4/2016 | Nikawa | |
| 2016/0215273 A1* | 7/2016 | Pasternack ........... | A61K 35/747 |

FOREIGN PATENT DOCUMENTS

WO    2018/026719 A1    2/2018

OTHER PUBLICATIONS

Schwenninger et al., Characterization of Low-Molecular-Weight Antiyeast Metabolites Produced by a Food-Protective Lactobacillus-Propionibacterium Coculture, Journal of Food Protection, vol. 71, No. 12, (2008), pp. 2481-2487.*
Sookkhee et al., Lactic acid bacteria from healthy oral cavity of Thai volunteers: inhibition of oral pathogens, Journal of Applied Microbiology, vol. 90, (2001), pp. 172-179.*
Anwar et al. (Dec. 2012) "Profile of candidiasis in HIV infected patients," Iranian Journal of Microbiology. 4(4):204-209.
Coman et al. (Aug. 2014) "In vitro evaluation of antimicrobial activity of Lactobacillus rhamnosus IMG 501, Lactobacillus paracasei IMG 502 and SYNBIO against pathogens," Journal of Applied Microbiology. 117(2):518-527.
Hasslof et al. (Jul. 2010) "Growth inhibition of oral mutans streptococci and candida by commercial probiotic lactobacilli—an in vitro study," BMC Oral Health. 10(18):1-6.
Rossoni et al. (Mar. 2017) "Lactobacillus paracasei modulates the immune system of Galleria mellonella and protects against Candida albicans infection," PLos One 12(3):1-17.
International Search Report with Written Opinion corresponding to International Patent Application No. PCT/US2017/044703, dated Oct. 20, 2017, 7 pages.
Abedin-Do et al. (Nov. 2015) "Immunomodulatory Effects of Lactobacillus Strains: Emphasis on their Effects on Cancer Cells", Immunotherapy, 7(12):1307-1329.
Aoudia et al. (2016) "Biofilms of Lactobacillus Plantarum and Lactobacillus Fermentum: Effect on Stress Responses, Antagonistic Effects on Pathogen Growth and Immunomodulatory Properties", Food Microbiology, 53(Pt A):51-59.

(Continued)

*Primary Examiner* — Jennifer M. H. Tichy
(74) *Attorney, Agent, or Firm* — Adler Pollock & Sheehan P.C.

(57) ABSTRACT

The invention provides a method and bacterial compositions for reducing or preventing an infection of a bodily tissue by a fungal microorganism by contacting the tissue with a composition comprising a purified *Lactobacillus paracasei* bacterium.

6 Claims, 11 Drawing Sheets
Specification includes a Sequence Listing.

(56) References Cited

OTHER PUBLICATIONS

Arvanitis et al. (Mar. 2013) "Invertebrate Models of Fungal Infection", Biochimica et Biophysica Acta, 1832(9):1378-1383.

Barbosa et al. (Mar. 2, 2016) "*Streptococcus* Mutans Can Modulate Biofilm Formation and Attenuate the Virulence of Candida Albicans", PLoS One, 11(3):16 pages.

Bergin et al. (Sep. 2003) "Fluctuations in Haemocyte Density and Microbial Load may be used as Indicators of Fungal Pathogenicity in Larvae of Galleria Mellonella", Microbes and Infection, 5(15):1389-1395.

Brown et al. (2009) "A Peptidomics Study Reveals the Impressive Antimicrobial Peptide Arsenal of the Wax Moth Galleria Mellonella", Insect Biochemistry and Molecular Biology, 39(11):792-800.

Chon et al. (2009) "Immunomodulatory Effects of Specific Bacterial Components of Lactobacillus Plantarum KFCC11389P on the Murine Macrophage Cell Line RAW 264.7", Journal of Applied Microbiology, 107(5):1588-1597.

Chon et al. (Dec. 2010) "Suppression of Proinflammatory Cytokine Production by Specific Metabolites of Lactobacillus Plantarum 10hk2 via Inhibiting NF-?B and p38 MAPK Expressions", Comparative Immunology, Microbiology and Infectious Diseases, 33(6):e41-e49.

Coronado-Castellote et al. (Dec. 2013) "Clinical and Microbiological Diagnosis of Oral Candidiasis", Journal of Clinical and Experimental Dentistry, 5(5):e279-e286.

Fallon et al. (Oct. 2011) "Pre-Exposure of Galleria Mellonella Larvae to Different Doses of Aspergillus Fumigatus Conidia Causes Differential Activation of Cellular and Humoral Immune Responses", Virulence, 2(5):413-421.

Galdeano et al. (Feb. 2006) "The Probiotic Bacterium Lactobacillus Casei Induces Activation of the Gut Mucosal Immune System Through Innate Immunity", Clinical and Vaccine Immunology, 13(2):219-226.

Ganz et al. (May 1995) "Defensins", Pharmacology & Therapeutics, 66(2):191-205.

Guarner et al. (Jul. 2012) "World Gastroenterology Organisation Global Guidelines: Probiotics and Prebiotics Oct. 2011", Journal of Clinical Gastroenterology, 46(6):468-481.

Hofs et al. (Mar. 2016) "Interaction of Candida Albicans with Host Cells: Virulence Factors, Host Defense, Escape Strategies, and the Microbiota", The Journal of Microbiology, 54(3):149-169.

Jorjao et al. (Nov. 2015) "Live and Heat-Killed Lactobacillus Rhamnosus ATCC 7469 May Induce Modulatory Cytokines Profiles on Macrophages RAW 264.7", The Scientific World Journal, 2015(716749):06 pages.

Kim et al. (Apr. 2006) "Probiotic Lactobacillus Casei Activates Innate Immunity via NF-kappaB and p38 MAP Kinase Signaling Pathways", Microbesand Infection, 8(4):994-1005.

Livak et al. (2001) "Analysis of Relative Gene Expression Data using Real-Time Quantitative PCR and the 2-Delta DeltaCT Method", Methods, 25:402-408.

Lowenberger, Carl (2001) "Innate Immune Response of Aedes Aegypti", Insect Biochemistry and Molecular Biology, 31(3):219-229.

Martínez-Álvarez et al. (Jan.-Mar. 2014) "The Immune Response Against *Candida* Spp. and Sporothrix Schenckii", Revista Iberoamericana de Micologia, 31(1):62-66.

Mayer et al. (Feb. 2013) "Candida Albicans Pathogenicity Mechanisms", Virulence, 4(2):119-128.

Mowlds et al. (2008) "Effect of Pre-Incubation Temperature on Susceptibility of Galleria Mellonella Larvae to Infection by Candida Albicans", Mycopathologia, 165(1):5-12.

Mylonakis et al. (Jul. 2005) "Galleria Mellonella as a Model System to Study Cryptococcus Neoformans Pathogenesis", Infection and Immunity, 73(7):3842-3850.

Peleg et al. (Sep. 23, 2008) "Prokaryote-Eukaryote Interactions identified by using Caenorhabditis Elegans", PNAS, 105(38):14585-14590.

Ryan et al. (2009) "Lactobacillus Salivarius Modulates Cytokine Induction and Virulence Factor Gene Expression in Helicobacter Pylori", Journal of Medical Microbiology, 58:996-1005.

Shai, Yechiel (Oct. 1999) "Mechanism of the Binding, Insertion and Destabilization of Phospholipid Bilayer Membranes by Alpha-Helical Antimicrobial and Cell Non-Selective Membrane-Lytic Peptides", Biochimica et Biophysica Acta, 1462(1-2):55-70.

Shai, Yechiel (2002) "Mode of Action of Membrane Active Antimicrobial Peptides", Biopolymers, 66(4):236-248.

Vilela et al. (Jan. 2015) "Lactobacillus Acidophilus ATCC 4356 Inhibits Biofilm Formation by C. Albicans and Attenuates the Experimental Candidiasis in Galleria Mellonella", Virulence, 6(1):29-39.

Vilmos et al. (Jun. 1998) "Insect Immunity: Evolutionary Roots of the Mammalian Innate Immune System", Immunology Letters, 62(2):59-66.

Wagner et al. (2012) "Probiotic Lactobacillus and Estrogen Effects on Vaginal Epithelial Gene Expression Responses to Candida Albicans", Journal of Biomedical Science, 19(58):08 pages.

Wickens et al. (Oct. 2008) "A Differential Effect of 2 Probiotics in the Prevention of Eczema and Atopy: A DoubleBlind, Randomized, Placebo-Controlled Trial", The Journal of Allergy and Clinical Immunology, 122(4):788-794.

Zdybicka-Barabas et al. (Sep. 2014) "Lysozyme and Defense Peptides as Suppressors of Phenoloxidase Activity in Galleria Mellonella", Archives of Insect Biochemistry and Physiology, 87(1):1-12.

\* cited by examiner

```
                             SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
tccagtccgt tttgttgttg                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
cagaggtgta attcgtcgca                                              20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
gaagatcgct ttcatagtcg c                                            21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
tactcctgca gttagcaatg c                                            21

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
acagagcgtg gctactcgtt                                              20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
gccatctcct gctcaaagtc                                              20
```

PROBIOTIC BACTERIA-DIRECTED PREVENTION OR TREATMENT OF FUNGAL INFECTION

CROSS-REFERENCES TO RELATED APPLICATIONS

This application is a national stage application filed under 35 U.S.C. § 371 of International Patent Application No. PCT/US2017/044703, filed Jul. 31, 2017, which claims the priority to and the benefit of priority under 35 U.S.C. § 119(e) to U.S. Provisional Application No. 62/369,735, filed Aug. 1, 2016, the entire contents of which are incorporated herein by reference for all purposes.

INCORPORATION BY REFERENCE TO THE SEQUENCE LISTING

The content of the text file named 21486-631001WO_ST25" which was created on Jul. 28, 2017 and is 1.45 kilobytes in size is hereby incorporated by reference in its entirety.

FIELD OF THE INVENTION

The invention relates to immune modulation.

BACKGROUND OF THE INVENTION

Among patients with Human Immunodeficiency Virus (HIV), *Candida albicans* infections continue to be a problem. Patients are plagued by persistent infections, with the oral cavity being a primary infection site. The fungi *C. albicans*, a natural colonizer of the human intestine, mouth, and skin, can cause conditions such as thrush: hallmarked by raised, white lesions in the mouth that cause pain. Providing patients with prophylactic antifungal chemotherapy can be suboptimal in the case of a chronic infection such as HIV. With continued prevalence of an antifungal such as fluconazole in the system, *C. albicans* can develop resistance, whereby the treatment can become further challenging. Among susceptible patients, persistent infections can lead to drug resistance due to the need for recurrent therapy.

SUMMARY OF THE INVENTION

The methods and compositions of the invention provide a solution to drawbacks of previous approaches to treat and prevent fungal infections. For example, the invention features a method of reducing or preventing an infection of a bodily tissue by a fungal microorganism by contacting the tissue with a composition comprising a purified *Lactobacillus paracasei* bacterium. The fungal microorganism can include *Candida albicans*. The bacterium or bacterial composition is preferably not substantially disseminated to lower gastrointestinal tissue. For example, the *L. paracasei* need not be ingested or is not ingested. For example, the *L. paracasei* is ingested less than 10%, 9%, 8%, 7%, 6%, 5%, 4%, 3%, 2%, 1%, 0.5%, 0.1% or less by weight). The composition is administered to or is applied to tissues of the oral cavity or adjacent tissues. For example, the tissues include mouth, lips, tongue, throat, or esophageal tissue. The tissue does not substantially comprise stomach or intestinal tissue.

In some examples, the fungal microorganism, e.g., pathogen, comprises *Candida albicans*. For example, the fungal microorganism is resistant to fluconazole. A subject to be treated may be immunocompromised, e.g., the subject had or has an HIV infection.

The *Lactobacillus paracasei* is purified. By "purified" or "substantially purified" is meant a *L. paracasei* bacterium that is substantially free of contaminating microorganisms or other macromolecules, e.g., polysaccharides, nucleic acids, or proteins. For example, the *L. paracasei* comprises strain 28.4. The bacterium or bacterial composition is in a form suitable for administration to oral cavity tissues, e.g., composition is in the form of a cream, liquid, or ointment for spreading on oral cavity tissues or in the form of a chewing gum, whereby oral cavity tissues are contacted with the bacteria as it is liberated from the gum or dissolvable or chewable tablet as the subject sucks on or chews the composition. Other formulations include a liquid mouth wash/rinse or spray to be applied to oral cavity tissues and associated tissues.

Also within the invention is a composition comprising a purified *Lactobacillus paracasei* bacterium and a gellan. For example, the composition is in the form of a cream ointment, or chewing gum or chewable tablet.

The terms "subject," "individual," and "patient" are used interchangeably herein to refer to a vertebrate, preferably a mammal, more preferably a human. The mammal can be e.g., a human or appropriate non-human mammal, such as primate, mouse, rat, dog, cat, cow, horse, goat, camel, sheep or a pig. The subject can also be a bird or fowl. Tissues, cells and their progeny of a biological entity obtained in vivo or cultured in vitro are also encompassed. As used herein, a "subject in need thereof" or "a patient" may be a subject having a HIV or a subject who had HIV. Alternatively, a subject may be a subject comprises a fungal pathogen that is resistant to an antifungal agent (other than the composition described herein), such as fluconazole.

As used herein, "treatment" or "treating," or "palliating" or "ameliorating" or "reducing" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term "lower gastrointestinal tissue" includes the lower gastrointestinal tract such as most of the small intestine and all of the large intestine. The gastrointestinal (GI) tract is conventionally divided into upper (mouth to ileum) and lower (cecum to anus). The lower digestive tract, also known as the bowel, is approximately 25 feet long and encompasses or consists of the small intestine and large intestine. Food from the stomach passes through the pyloric valve into the small intestine, a 20-foot tube with three sections: the duodenum, the jejunum, and the ileum. In some clinical contexts, e.g., gastrointestinal bleeding, the demarcation between the upper and lower GI tract is the duodenojejunal (DJ) junction (ligament of Treitz All publications and patents mentioned herein are hereby incorporated by reference in their entirety as if each individual publication or patent was specifically and individually indicated to be incorporated by reference. In case of conflict, the present application, including any definitions herein, will control.

BRIEF DESCRIPTION OF THE DRAWINGS

FIG. 2. *L. paracasei* strain 28.4 prolonged survival of *G. mellonella* larvae infected with *C. albicans*.

DETAILED DESCRIPTION

Figure 1:
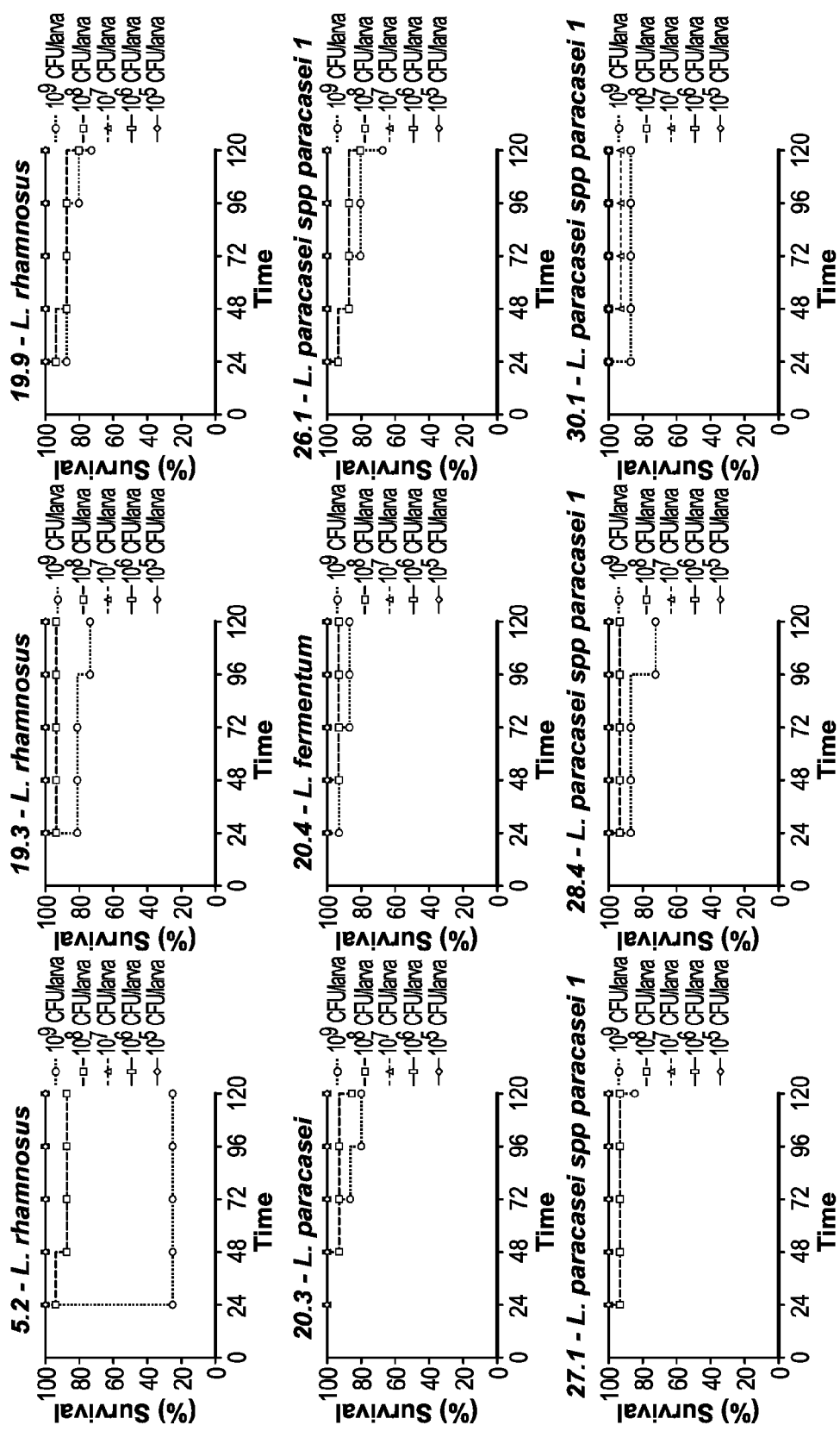
FIG. 1 is a series of line graphs showing susceptibility of *G. mellonella* to infection with *Lactobacillus* spp. Serial concentrations of *Lactobacillus*/larvae were delivered to observe the effects to larvae longevity.

Recurrent fungal infections are a problem in immunocompromised subjects, e.g., those infected with HIV, those suffering from autoimmune diseases including diabetes, those with immune systems weakened from the disease and/or from treatments for disease such as chemotherapy and radiation used for treatment of cancer, and the elderly whose immune system may be weakened from age.

Oral thrush, also called oral candidiasis is a condition in which the fungus, *Candida albicans*, accumulates on the lining of the mouth. *Candida* is a normal organism in the mouth, but sometimes it can overgrow and cause clinical symptoms. Oral thrush causes creamy white lesions, usually on the tongue or inner cheeks. Sometimes oral thrush may spread to the roof of the mouth, gums or tonsils, or the back of the throat. Although oral thrush can affect anyone, it's more likely to occur in babies, the elderly, and in people with suppressed immune systems or those who take certain medications as described above.

We sought to address the problem of recurrent infection by looking for a non-drug method of treatment. The use of probiotics has been successfully used to influence gut colonization. Thus, we endeavored to determine if bacteria could affect *C. albicans*. We previously found that prokaryotic-eukaryotic interactions can inhibit *C. albicans*, in particular the ability to form hyphae (Peleg et al. PNAS. 2008; 105(38):14585-14590; Vilela et al., Virulence. 2015; 6(1): 29-39). Knowing that bacteria can directly influence *C. albicans* we searched for a strain of *Lactobacillus*, a bacterium that can be used as a probiotic, that is native to the oral cavity and can inhibit a *C. albicans* infection. To this end, we generated a collection of *Lactobacillus* strains derived from the oral cavity of HIV patients in Brazil. We then determined if any of the collected species could inhibit *C. albicans*.

The data described herein identified a species that is superior to other *Lactobacillus* in inhibiting *C. albicans* infections: *Lactobacillus* paracasei strain 28.4 (ATCC accession number assigned Patent Deposit Number PTA-126984 of *Lactobacillus* paracasei, deposited on Feb. 16, 2021 at the American Type Culture Collected (ATCC) in Manassas, Va. 20110), providing prophylactic protection. Using an invertebrate infection model, the greater wax moth, *Galleria mellonella* exhibited prolonged survival when *L. paracasei* 28.4 was provided prior to a lethal dose of *C. albicans*. Our interrogation of how *Lactobacillus* affects the host found it is able to modulate the immune response of *G. mellonella*, providing protection against *C. albicans* infection. This result is mediated by recruitment of circulating hemocytes and the production of elevated levels of antimicrobial peptides (AMP's), which protect the insect exposure to the pathogen, The human mouth is naturally colonized by a multitude of microbes. When individuals become immunocompromised, they can become susceptible to this reservoir of microbes. We collected bacterial samples from the oral cavity of HIV patients in an effort to identify *Lactobacillus* strains that could provide protection against infectious fungal microbes, serving as a probiotic. Others have used the idea of providing probiotics to prevent dental cavities using *Lactobacillus acidophilus* to inhibit the bacteria *Streptococcus mutans*. By contract, we are using a different *Lactobacillus* species to inhibit *C. albicans*.

In order to evaluate the hypothesis that bacteria of the genus *Lactobacillus* have the ability to be immunomodulatory, we first evaluated whether some *lactobacilli* from our collection can prolong survival after infection with *C. albicans*. Since there are no studies in the literature inoculating *L. paracasei*, *L. fermentum* and *L. rhamnosus* in *G. mellonella*, we first evaluated the susceptibility of *G. mellonella* to infection with *Lactobacillus* ssp. In this series of experiments, we tested concentrations between $10^5$-$10^9$ cells/larva, and only in the 2 highest concentrations ($10^8$ and $10^9$ cells/larvae) did we observe larval death.

Lactobacillus paracasei

*L. paracasei* is a gram-positive, facultatively heterofermentative, non-spore forming microorganism in the family of lactic acid bacteria. The cells of *L. paracasei* are typically rod shaped, with a size range of 2.0 μm to 4.0 μm in width, and 0.8 to 1.0 μm in length. The organism is nonmotile. *L. paracasei* cells often have square ends, and may exist either in single form or in chains. A number of different strains of *L. paracasei* have been isolated from a variety of environments including dairy, plants, and human and animal gastrointestinal tracts. *L. paracasei* is genotypically and phenotypically indistinguishable from other members of its genus such as *Lactobacillus casei* and *Lactobacillus rhamnosus*. However, they are easily differentiated from each other by their fermentation profiles. *L. paracasei* grows optimally in a temperature range between 10 and 37° C.

Example 1

*Lactobacillus paracasei* Modulates the Immune System of *Galleria mellonella* and Protects Against *Candida albicans* Infection Probiotics can control opportunistic infectious due to their ability to stimulate the immune system. Using the non-vertebrate model host *Galleria mellonella*, we evaluated whether *Lactobacillus* spp. are able to modulate the immune system and provide protection against *Candida albicans* infection. Among different strains of *Lactobacillus paracasei*, *Lactobacillus rhamnosus* and *Lactobacillus fermentum*, we verified that *L. paracasei* 28.4 strain had the greatest ability to prolong the survival of larvae infected with a lethal dose of *C. albicans*. We found that the injection of $10^7$ cells/larvae of *L. paracasei* into *G. mellonella* larvae infected by *C. albicans* increased the survival of these animals in 50% compared to the control group.

The immune mechanisms involved in the protection against *C. albicans* infection were investigated, evaluating the number of hemocytes and the gene expression of antifungal peptides. We found that *L. paracasei* increased the hemocyte density ($2.38\times10^6$ cells/mL) in relation to the control group ($1.29\times10^6$ cells/mL), indicating that this strain is capable to recruit hemocytes into the *G. mellonella* hemolymph. Further, we found that the *L. paracasei* upregulated the genes that encode the antifungal peptides galiomicin and gallerymicin. In relation to the control group, *L. paracasei* induced an increase of gene expression of 6.67-fold for galiomicin and of 17.29-fold for gallerymicin. These data indicate that *L. paracasei* modulates the immune system of *G. mellonella* in an insect model of *C. albicans* and therefore indicates that this probiotic strain is useful to reduce the severity of and protect against candidiasis in mammalian subjects such as humans.

Probiotics to Reduce Infection by Fungal Pathogens

*C. albicans* is a commensal yeast that colonizes the gastrointestinal track in approximately 53% of healthy individuals (Coronado-Castellote L, Jimenez-Soriano Y. 2013. J Clin Exp Dent 5:e279-286). This yeast is an opportunistic pathogen that can cause severe and recurrent infections in the mucosa, as well as life-threatening systemic infections (Mayer F L, Wilson D, Hube B. 2013. Virulence 4:119-128). The development of mucosa or systemic candidiasis occurred frequently in immunosuppressed patients (Martinez-Alvarez J A, Perez-Garcia L A, Flores-Carreon A, Mora-Montes H M. 2014. Rev Iberoam Micol 31:62-66) and is associated with a complex interplay between the fungal virulence factors and the host immune system (Hofs S, Mogavero S, Hube B. 2016. J Microbiol 54:149-169). The host response to *C. albicans* is characterized by a rapid activation of the innate immune system upon first contact with the fungal cell. During the innate immune response, macrophages, neutrophils and dendritic cells provide primary protective effect via direct antifungal activities, including phagocytosis and release of antimicrobial peptides. The activation of the innate immune system is the basis for a more specific immune response mediated by T or B lymphocytes (adaptative immune system) (4, 5).

Probiotics bacteria have been studied as a potential method for prevent opportunistic infectious diseases due to their ability to stimulate the immune system (Wickens K, Black P N, Stanley T V, Mitchell E, Fitzharris P, Tannock G W, Purdie G, Crane J, Probiotic Study G. 2008. J Allergy Clin Immunol 122:788-794; Ryan K A, O'Hara A M, van Pijkeren J P, Douillard F P, O'Toole P W. 2009. *Lactobacillus*. J Med Microbiol 58:996-1005; Jorjao A L, de Oliveira F E, Leao M V, Carvalho C A, Jorge A O, de Oliveira L D. 2015. ScientificWorldJournal 2015:716749). According to World Health Organization probiotics, are live microorganisms that confer health benefits on the host when administered in adequate amounts (Guarner F, Khan A G, Garisch J, Eliakim R, Gangl A, Thomson A, Krabshuis J, Lemair T, Kaufmann P, de Paula J A, Fedorak R, Shanahan F, Sanders M E, Szajewska H, Ramakrishna B S, Karakan T, Kim N, World Gastroenterology O. 2012. World Gastroenterology Organisation Global Guidelines: probiotics and prebiotics October 2011. J Clin Gastroenterol 46:468-481). In this context, several *Lactobacillus* strains have been investigated as a probiotic bacterium to inhibit the colonization of pathogens and to stimulate the immune system (Aoudia N, Rieu A, Briandet R, Deschamps J, Chluba J, Jego G, Garrido C, Guzzo J. 2016. Food Microbiol 53:51-59). Different *lactobacilli* strains can modulate innate and adaptive immune system preventing the initiation and progression of cancer cells (Abedin-Do A, Taherian-Esfahani Z, Ghafouri-Fard S, Ghafouri-Fard S, Motevaseli E. 2015. Immunotherapy 7:1307-1329). Moreover, other previous studies showed that certain strains of *lactobacilli* were capable to modulate the expression of several genes involved in the regulation of the immune system (Chon H, Choi B, Jeong G, Lee E, Lee S. 2010. Comp Immunol Microbiol Infect Dis 33:e41-49; Chon H, Choi B, Lee E, Lee S, Jeong G. 2009. J Appl Microbiol 107:1588-1597; Galdeano C M, Perdigon G. 2006. Clin Vaccine Immunol 13:219-226; Kim Y G, Ohta T, Takahashi T, Kushiro A, Nomoto K, Yokokura T, Okada N, Danbara H. 2006. Microbes Infect 8:994-1005; Wagner R D, Johnson S J. 2012. J Biomed Sci 19:58).

The study of immune response against *C. albicans* was performed in a *Galleria mellonella* model that is an art-recognized tool to the study of innate immune response. The immune system of *G. mellonella* demonstrates a number of structural and functional similarities to the innate immune system of mammals (Vilmos P, Kurucz E. 1998. Immunol Lett 62:59-66) and is composed by cellular and humoral components (Fallon J P, Troy N, Kavanagh K. 2011. Virulence 2:413-421). Their cellular immune response consists of the synthesis and mobilization of immune cells called hemocytes, which can surround and engulf invading pathogens (Mowlds P, Kavanagh K. 2008. Mycopathologia 165: 5-12). The humoral element of these larvae consists in the production of a wide range of antimicrobial peptides (AMP) (Ganz T, Lehrer R I. 1995. Pharmacol Ther 66:191-205; Zdybicka-Barabas A, Mak P, Jakubowicz T, Cytrynska M. 2014. Arch Insect Biochem Physiol 87:1-12). In addition, *G. mellonella* is a facile infection model that have been used as a screening tool for studies using vertebrate models (Barbosa J O, Rossoni R D, Vilela S F, de Alvarenga J A, Velloso Mdos S, Prata M C, Jorge A O, Junqueira J C. 2016. PLoS One 11:e0150457). Prophylactic or therapeutic inoculation of *L. acidophilus* ATCC 4356 into *G. mellonella* infected by *C. albicans* reduced the number of yeast cells in the larval hemolymph and increased the survival of these animals (Barbosa J O, Rossoni R D, Vilela S F, de Alvarenga J A, Velloso Mdos S, Prata M C, Jorge A O, Junqueira J C. 2016. PLoS One 11:e0150457).

Due to the high recurrence of *Candida* spp. lesions in immunosuppressed patients, the continuous prophylactic use of probiotics to prevent *Candida* spp. infections represents a potential strategy in thwarting recurrent infections. Using *G. mellonella* as a model for the study of immunomodulatory effects of probiotics, we screened different clinical strains of *Lactobacillus* in order to identify new probiotics strains capable to prevent candidiasis. Since *L. paracasei* strain 28.4 showed the greatest ability to reduce *Candida* infections, we identified a number of insect immune responses to evaluate its probiotic activity. Based on these investigations, we were able to describe the specific responses stimulated by *L. paracasei* 28.4 that protected *G. mellonella* against *C. albicans* infections.

The following materials and methods were used to generate the data described herein.

Organisms and strains. In this study we used 9 clinical strains of *Lactobacillus* spp. recovered from the oral cavity and 1 reference strain of *C. albicans* from the American Type Culture Collection (ATCC 18804). The oral *Lactobacillus* spp. strains were isolated from the saliva of 41 healthy patients and included: *L. paracasei* (n=5), *Lactobacillus rhamnosus* (n=3) and *Lactobacillus fermentum* (n=1) (Table 1). All the strains were stored as frozen stocks with 25% glycerol at −80° C. until used.

TABLE 1

Clinical strains of *Lactobacillus* used in this study

| Species | Strain designation |
| --- | --- |
| L. fermentum | 20.4 |
| L. paracasei | 20.3 |
| L. paracasei | 26.1 |
| L. paracasei | 27.1 |
| L. paracasei | 28.4 |
| L. paracasei | 30.1 |
| L. rhamnosus | 5.2 |
| L. rhamnosus | 19.3 |
| L. rhamnosus | 19.9 |

Microbial inoculum preparation. *C. albicans* cells were grown in YPD medium (1% yeast extract, 2% bacto-peptone, 2% dextrose) overnight at 30° C. with agitation. Cells were collected by centrifugation and washed 3 times with PBS. Yeast cells were counted using a hemocytometer. The cell number was confirmed by determining CFU/mL on YPD plates. *Lactobacillus* spp. were grown in *Lactobacillus* MRS Broth (Difco, Detroit, USA) for 24 h at 37° C. in a bacteriological incubator under microaerophilic conditions. Cells were collected by centrifugation and washed 3 times with PBS, after this the number of cells in suspension was determined with a spectrophotometer (Eppendorf Biophotometer Plus, Eppendorf, Hamburg, Germany). For the assay with heat-killed (HK) *Lactobacillus* spp., we incubated bacteria at 80° C. for 20 min and subsequently plated the cells on MRS agar to ensure that no viable cells remained.

*G. mellonella* survival. For this study, the standard methodologies described by Mylonakis et al. (Mylonakis E, Moreno R, El Khoury J B, Idnurm A, Heitman J, Calderwood S B, Ausubel F M, Diener A. 2005. Infect Immun 73:3842-3850) and Vilela et al. (Barbosa J O, Rossoni R D, Vilela S F, de Alvarenga J A, Velloso Mdos S, Prata M C, Jorge A O, Junqueira J C. 2016. PLoS One 11:e0150457) were used. *G. mellonella* (Vanderhorst Wholesale, St.

Marys, Ohio) in their final larval stage were stored in the dark and used within 7 days from shipment. Sixteen randomly chosen *G. mellonella* larvae with similar weight and size (250-350 mg) were used per group in all assays. Two control groups were included in the assays that form part of this study: one group was inoculated with PBS, and the other received no injection as a control for general viability.

We initially determined the sub-lethal inoculum concentration of *Lactobacillus* by injecting larvae with serial dilutions of the bacteria. For this purpose, different concentrations of each *Lactobacillus* strain ($10^5$ to $10^9$ cells/larvae) were inoculated into *G. mellonella* through the last left proleg. The larvae were kept on Petri dishes at 37° C. and monitored daily for survival.

To evaluate the effects of probiotics on *C. albicans* infections, the larvae were pre-infected with *Lactobacillus* by injecting the bacteria (concentration previously determined) through the last left proleg. After 1 h, larvae were infected with $10^6$ cells/larvae of *C. albicans* suspended in PBS at the last right proleg. Larvae were incubated at 37° C. and monitored daily for survival. The experimental groups used in this study are presented in Table 2. Among all the strains tested, *L. paracasei* 28.4 reached the highest survival rate and it was selected for the following experiments.

TABLE 2

Experimental groups used to evaluate the effects of *Lactobacillus* strains on *Candida* infections

| Groups | $1^{st}$ Injection (Last left proleg) | $2^{nd}$ Injection (Last right proleg) |
|---|---|---|
| PBS | PBS | PBS |
| C. albicans | PBS | C. albicans |
| Lactobacillus | Lactobacillus | PBS |
| Lactobacillus + C. albicans | Lactobacillus | C. albicans |
| No Injection | — | — |

Evaluating *G. mellonella* hemocyte density. Larvae were pre-infected with *L. paracasei* strain 28.4 by injecting the bacteria at the last left proleg. After 1 h, larvae were infected with *C. albicans* at the last right proleg. Hemocytes were collected from the hemocoel at 4 h post-injection with *C. albicans*. Larvae were bled into tubes containing cold, sterile insect physiologic saline (IPS) (150 mM sodium chloride; 5 mM potassium chloride; 100 mM Tris-hydrochloride, pH 6.9 with 10 mM EDTA, and 30 mM sodium citrate). The hemocytes were enumerated using a hemocytometer and the results were averaged from four replicates.

Analysis of peptide expression. Larval RNA was extracted using a TRIzol (Ambion, Inc., Carlsbad, Calif., USA) as recommended by the manufacturer at 4, 8, and 24 h post-injection of *L. paracasei* strain 28.4. In brief, a 2 mL volume of TRIzol was added to a 15 mL tube containing the homogenized frozen tissue of larvae and incubated at room temperature (RT) for 10 min. Subsequently, 400 µL of chloroform (Sigma-Aldrich, St. Louis, Mo., USA) was added and the tubes were centrifuged at 12,000×g for 15 min at 4° C. The supernatant was then transferred to a new tube, and 1 mL of isopropanol (Sigma-Aldrich, St. Louis, Mo., USA) was added. After centrifugation, the obtained pellet was washed with 70% ethanol (Sigma-Aldrich, St. Louis, Mo., USA), centrifuged again, and suspended in 50 µL of nuclease-free water (Ambion Inc., Carlsbad, Calif., USA). The concentration, purity and quality of the RNA were verified using a NanoVue Plus spectrophotometer (GE Healthcare Bio-Sciences, Pittsburgh, USA).

The extracted total RNA (1 µg) was transcribed into complementary DNA (cDNA) using the Verso cDNA Synthesis Kit (Thermo Fisher Scientific Inc, Waltham, Mass., USA), according to the protocols recommended by the manufacturer. The primers for the gene encoding gallerymicin were described and used as indicated by Bergin et al. (25) (Table 3). The transcribed cDNAs were amplified for relative quantification of the expression of the genes encoding galiomicin and gallerymicin in relation to the concentration of the reference gene (β-actin).

TABLE 3

PCR primer pairs used to amplify regions of the genes involved in the immune system of *G. mellonella* and a reference gene

| Gene Name | Sequence 5'-3' | bp* | Reference |
|---|---|---|---|
| Galiomicin F[a] | TCCAGTCCGTTTTGTTGTTG (SEQ ID NO: 1) | 123 | This study |
| Galiomicin R[b] | CAGAGGTGTAATTCGTCGCA (SEQ ID NO: 2) | 123 | This study |
| Gallerymicin F[a] | GAAGATCGCTTTCATAGTCGC (SEQ ID NO: 3) | 175 | Bergin et al. (25) |
| Gallerymicin R[b] | TACTCCTGCAGTTAGCAATGC (SEQ ID NO: 4) | 175 | Bergin et al. (25) |
| β-actin F[a] | ACAGAGCGTGGCTACTCGTT (SEQ ID NO: 5) | 104 | This study |
| β-actin R[b] | GCCATCTCCTGCTCAAAGTC (SEQ ID NO: 6) | 104 | This study |

[a]F indicates a forward primer
[b]R indicates a reverse primer
*Base pair (Fragment size)

The qPCR method was applied to evaluate the amount of the cDNA products in the exponential phase of the amplification reaction. As a detection system, the iTaq™ Universal SYBR® Green Supermix (Bio-Rad Laboratories, Inc, Hercules, Calif., USA) was used in the following reaction mixture: 5 µL of iTaq Universal SYBR Green (2×), 300 nM of the forward primer, 300 nM of the reverse primer, 2 µL of cDNA solution (diluted 1:10) and 2 µL of nuclease-free water (Ambion Inc., Carlsbad, Calif., USA), to obtain a final volume of 10 µL in each well of a 96-well plate (Bio-Rad Laboratories, Inc, Hercules, Calif., USA). As a negative control for the reaction, all the reagents were added to the last wells of the plates except for cDNA, and the wells were sealed with optical adhesive (Bio-Rad Laboratories, Inc, Hercules, Calif., USA). Subsequently, the plate was placed in a CFX96 Touch™ Real-Time PCR Detection System (Bio-Rad Laboratories, Inc, Hercules, Calif., USA) device. The following cycling parameters were used: 95° C. for 2 min for an initial denaturation followed by 40 cycles of 95° C. for 15 s and 60° C. for 30 s. After the end of the last cycle, the samples were subjected to dissociation (melting) curve analysis, and the absence of any bimodal curve or abnormal amplification signal was observed and analyzed every 0.1° C. The $2^{-\Delta\Delta CT}$ method was used to analyze the relative changes in gene expression from the quantitative RT-PCR experiment (Livak K J, Schmittgen T D. 2001. Methods 25:402-408).

Quantification of Candida CFU/larvae in G. mellonella hemolymph. The methodology described by Vilela et al. was used with some modifications. Larvae were infected with the same method used for the Galleria mellonella survival assay. For quantification of the presence of C. albicans in infected G. mellonella, the larvae were euthanized 4, 8 and 24 h after infection in the following groups: PBS+C. albicans and 28.4+C. albicans. A pool of 4 larvae was used per group and time. The experiment was carried out in triplicate using 16 larvae per group, for a total of 96 infected larvae. A control group was included for each time point, which was injected with 10 µL PBS into the last left proleg.

At each time point, the larvae were cut in the cephalo-caudal direction with a scalpel blade and squeezed to remove the hemolymph, which was transferred to an Eppendorf tube. Serial dilutions were prepared from the hemolymph pool, seeded onto Petri dishes containing Sabouraud dextrose agar (Difco, Detroit, USA) supplemented with chloramphenicol (100 µg/mL), and incubated for 48 h at 37° C. After this period, the colonies were counted for the calculation of CFU/larvae.

Statistical analysis. Percent survival and killing curves of G. mellonella were plotted and statistical analysis was performed by the Kaplan-Meier test using GraphPad Prism statistical software (GraphPad Software, Inc., California, CA, USA). Analysis of variance (ANOVA) was used to compare the results obtained in the survival assays. Student's t-test was used to compare hemocyte densities. A P value≤0.05 was considered significant.

Effects of Lactobacillus spp. on Experimental Candidiasis

In order to evaluate whether bacteria of the genus Lactobacillus have immunomodulatory effects and to identify potential probiotic strains for the prevention of Candida infections, we analyzed different Lactobacillus clinical strains from our collection including some strains of L. fermentum, L. paracasei and L. rhamnosus.

Firstly, we evaluated the susceptibility of G. mellonella to Lactobacillus strains using larvae no infected by C. albicans for determining the sub-lethal inoculum concentration. We tested concentrations ranging $10^5$ to $10^9$ cells/larva and death of larvae was observed only with the two highest concentrations ($10^8$ and $10^9$ cells/larvae) (FIG. 1).

Based on these results, a sub-lethal concentration of $10^6$ cells/larva was adopted for the study of the effects of Lactobacillus strains on experimental candidiasis. We screened 9 clinical strains of lactobacilli to determine which strain(s) prolonged survival after infection with C. albicans. In the control group, the infection with C. albicans without previous injection of lactobacilli caused death in 100% of the larvae within 24 h. When the larvae were pretreated with Lactobacillus spp. prior to C. albicans infection, the survival rate of G. mellonela larvae was dependent on the Lactobacillus strain injected. Among the 9 strains analyzed, 6 were capable to prolong the survival of larvae infected with C. albicans by up to 120 h (Table 4). Using an ANOVA test to compare all the Lactobacillus strains, we found that L. paracasei strain 28.4 reached the greatest survival rate with statistically significant difference compared to other strains. Then, this strain was selected for all the subsequent assays.

TABLE 4

Effects of Lactobacillus spp. on experimental candidiasis based on the analysis of survival curves of G. mellonella larvae

| Strain | Survival after 120 h (%) |
|---|---|
| 20.4 - L. fermentum | 0 |
| 20.3 - L. paracasei | 12 |
| 26.1 - L. paracasei | 19 |
| 27.1 - L. paracasei | 6 |
| 28.4 - L. paracasei | 27 |
| 30.1 - L. paracasei | 0 |
| 5.2 - L. rhamnosus | 14 |
| 19.3 - L. rhamnosus | 0 |
| 19.9 - L. rhamnosus | 14 |

Figure 2A:
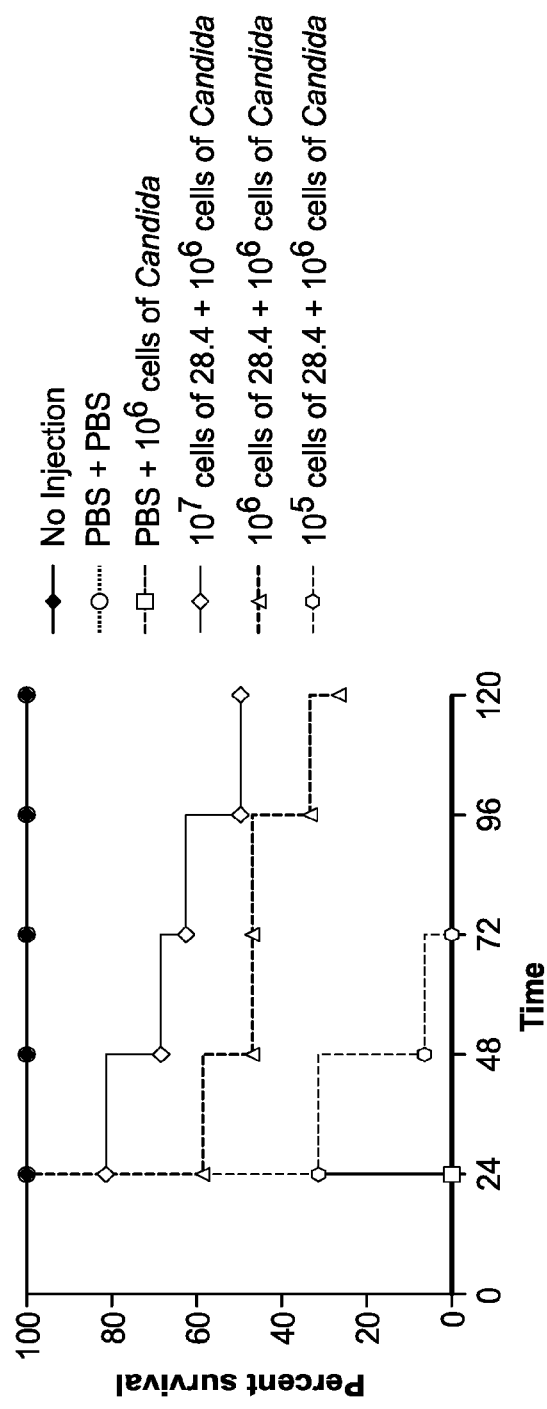
FIG. 2A is a line graph showing the survival rate for different concentrations of *L. paracasei*: significant differences were observed for the groups $10^5$ cells of 28.4+*Candida* ($p=0.0166$), $10^6$ cells of 28.4+*Candida* ($p=0.0003$) and $10^7$ cells of 28.4+*Candida* ($p=0.0001$) in relation to the control group (PBS+$10^6$ cells of *Candida*).
Figure 2B:
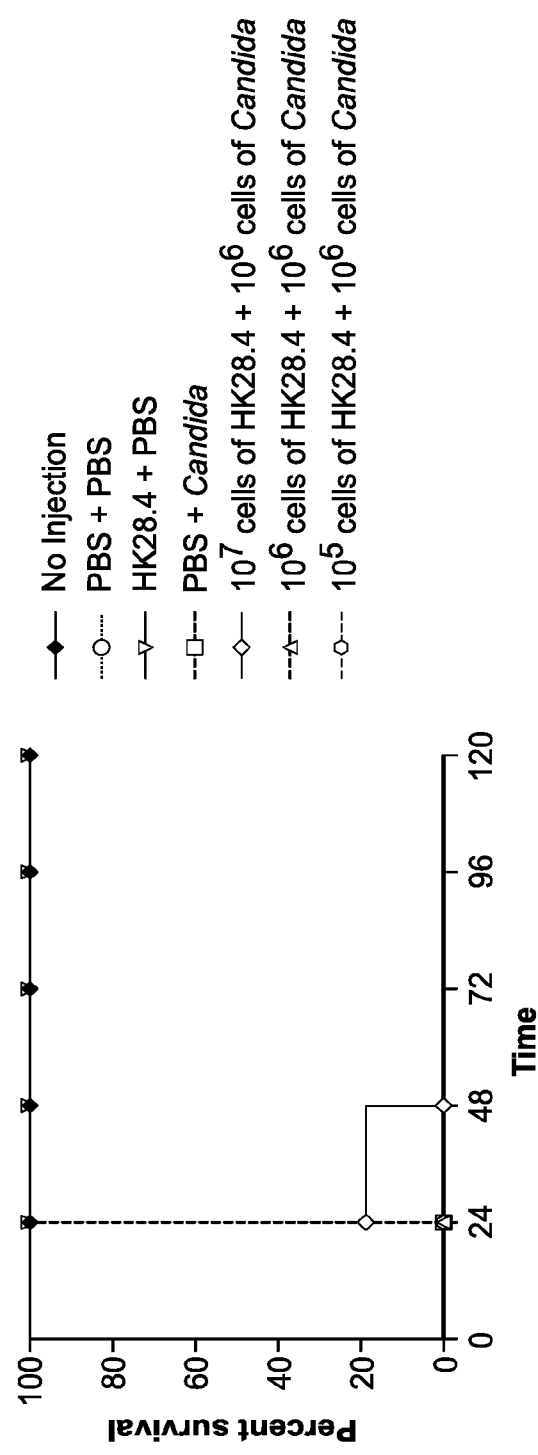
FIG. 2B is a line graph showing the survival rate for Heat-Killed (HK) *L. paracasei*: no significant statistically differences were observed for the groups $10^5$ cells of HK28.4+*Candida* ($p=1.000$), $10^6$ cells of HK28.4+*Candida* ($p=1.000$) and $10^7$ cells of HK28.4+*Candida* ($p=0.0733$) when compared to the control group PBS+*Candida*. Kaplan-Meier test, $p \leq 0.05$.

In order to determine whether different concentrations of L. paracasei strain 28.4 could influence the survival rate of larvae infected with C. albicans, the larvae were pretreated with L. paracasei at concentrations of $10^5$-$10^7$ cells/larva. We observed a dose dependent survival rate of the larvae, whereby an inoculum of $10^7$ cells/larva of L. paracasei reached higher survival rate in relation to the other concentrations ($10^5$ and $10^6$ cells/larvae) (FIG. 2A). The increase of the L. paracasei concentration was correlated with a decrease of the melanization of G. mellonella, that is part of the infection process with C. albicans (FIG. 5-1 to 5-4). In addition, we evaluated if the survival rate of G. mellonella could be influenced by the viability of L. paracasei strain 28.4. We used the same groups described above, but live L. paracasei was replaced by heat-killed L. paracasei. Heat-killed L. paracasei did not provide prophylactic protection, and thus did not increase the survival G. mellonella infected with C. albicans. These data indicate that the probiotic action was a consequence of the living and not dead bacteria (FIG. 2B).

Effects of L. paracasei Strain 28.4 on G. mellonella Hemocyte Density

Figure 3:
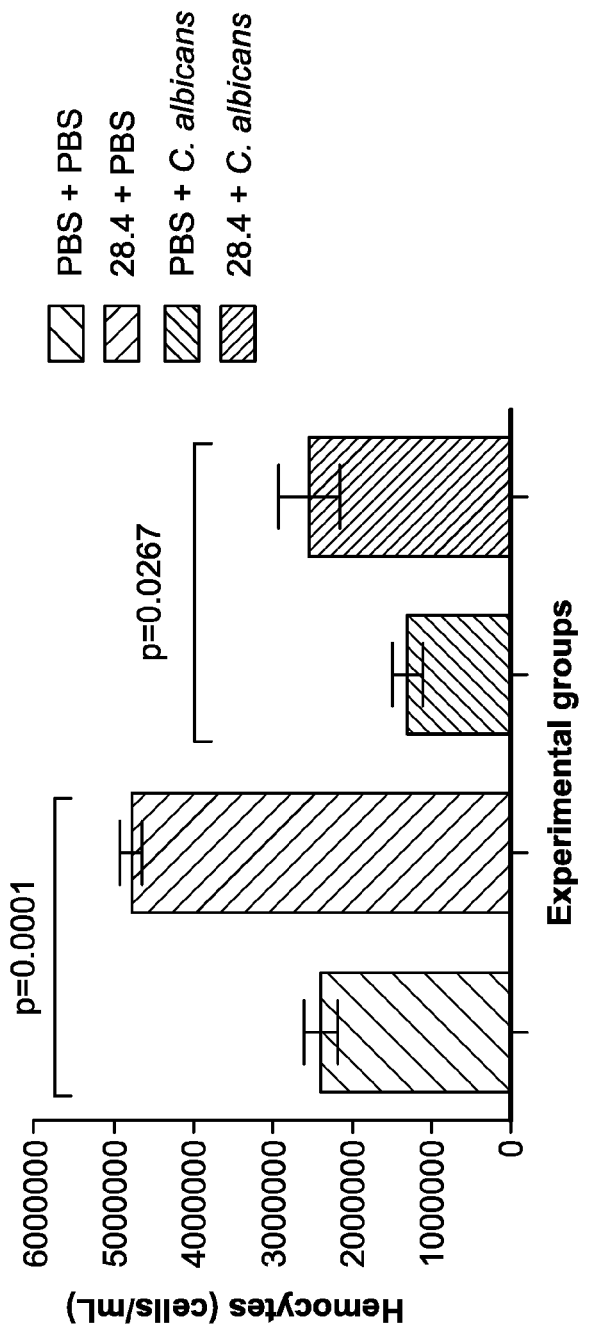
FIG. 3 is a bar graph showing *G. mellonella* hemocyte density increased with the injection of *L. paracasei* strain 28.4. Hemocyte density of *L. paracasei* group (28.4+28.4) increased $2.38 \times 10^6$ more cells/mL compared to a PBS control (PBS+PBS). The group *L. paracasei*+*C. albicans* (28.4+ *C. albicans*) also increased the hemocyte density $1.24 \times 10^6$ more cells/mL compared to *C. albicans* group (PBS+*C. albicans*). Student t test, $p \leq 0.05$ value was considered significant. **$p=0.0001$, *$p=0.0267$.

To investigate the immune mechanisms associated with the preventive effects of L. paracasei against Candida infection, we determined the number of available hemocytes in the hemolymph of larvae after 4 h of Lactobacillus injection. As the higher survival rate of G. mellonella was achieved with a concentration of $10^7$ cells/larvae of L. paracasei, we used this concentration to the hemocyte density assay. Firstly, we analyzed only the larvae not infected by C. albicans. The hemocyte density in the L. paracasei group increased the number of cells compared to the PBS control group (2-fold increase). In the larvae infected with C. albicans, the group pretreated with L. paracasei also increased the hemocyte density compared to C. albicans control group (1.96-fold increase) (FIG. 3).

These results indicate that *L. paracasei* strain 28.4 recruits hemocytes into the hemolymph and protect *G. mellonella* against *Candida* infections.

Effects of *L. paracasei* Strain 28.4 on the Expression of the Gene Encoding Gallerymicin and Galiomicin The presence of an increased hemocyte density indicates that *L. paracasei* strain 28.4 modulates the immune response of *G. mellonella* larvae. Thus, we further explored alterations in the immune response examining the expression of antifungal peptides. Using RT-PCR, we evaluated the change in expression of the gene encoding galiomicin, a defensin identified in *G. mellonella*, and gallerymicin, a cysteine-rich antifungal peptide.

Figure 4A:
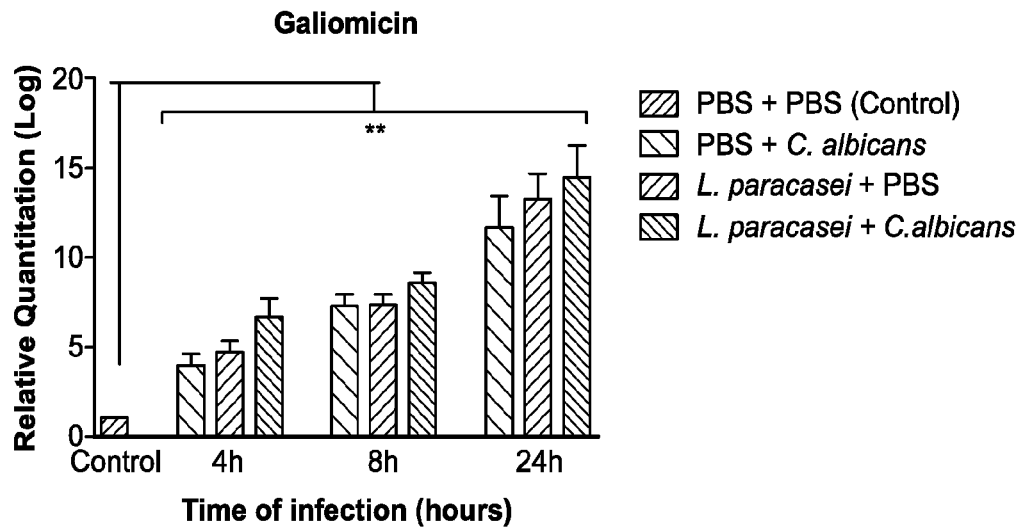
FIGS. 4A and B are bar graphs showing that. *L. paracasei* strain 28.4 increased the expression of antifungal peptides of *G. mellonella*. Relative quantification (log) of Galiomicin (FIG. 4A) and Gallerymicin (FIG. 4B) compared from larvae treated with only PBS (Control) to larvae pre-treated with PBS and infected with *C. albicans*, larvae only treated with *L. paracasei*, and larvae pre-treated with *L. paracasei* and infected with *C. albicans*. Values are expressed as the means and standard deviation. ANOVA and Tukey Tests ($p \leq 0.05$). ***$p \leq 0.001$.

We found that *L. paracasei* strain 28.4 increased the expression of both antifungal peptides analyzed. For the gene encoding galiomicin, the group pretreated with *L. paracasei* and then infected with *C. albicans* had a statistically significant increase (p=0.0001) in relation to the control group (PBS+*C. albicans*) only for the observation time of 4 h. *L. paracasei* leaded an increase of gene expression of 6.67 and 1.68-fold compared, respectively, to the control group formed by PBS+PBS and the control group composed by PBS+*C. albicans* (FIG. 4A).

Figure 4B:
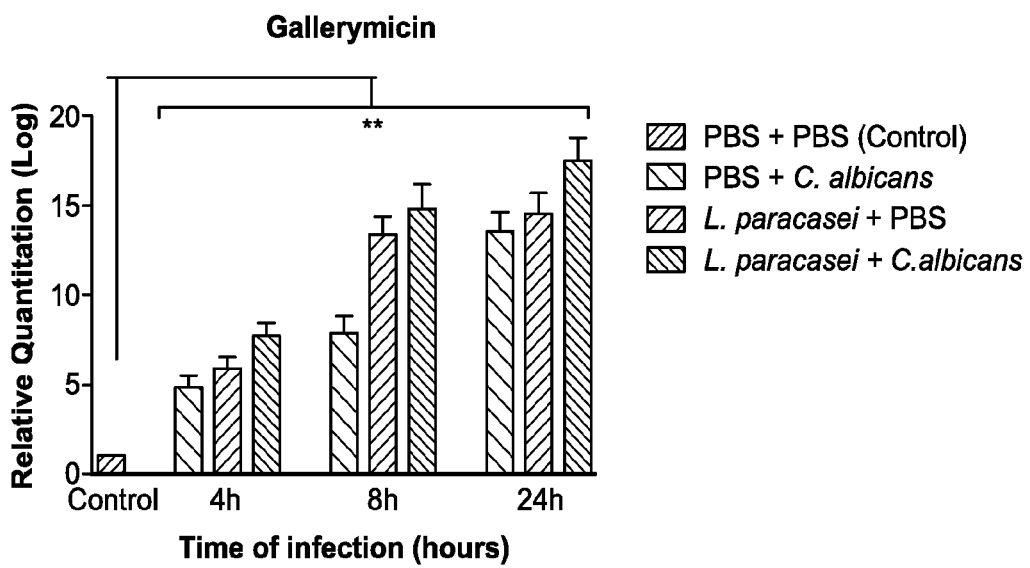
Figure 5A:
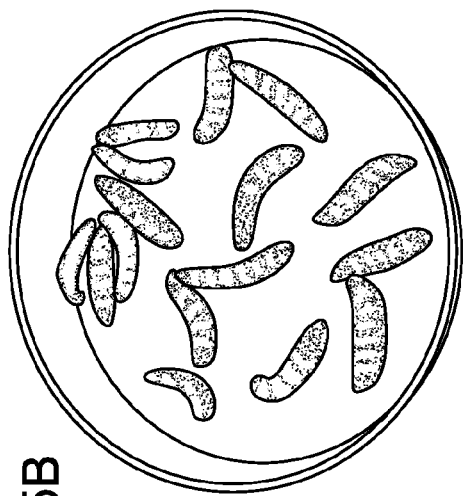
FIGS. 5A-5D are photographs showing *G. mellonella* larvae. Analyses of melanization process after 24 h of prophylactic treatment with *L. paracasei* and infection with *C. albicans*: control group treated with PBS (FIG. 5A), group treated with $10^5$ cells/larva of *L. paracasei* (FIG. 5B), group treated with $10^6$ cells/larva of *L. paracasei* (FIG. 5C), and group treated with $10^7$ cells/larva of *L. paracasei* (FIG. 5D).
Figure 5B:
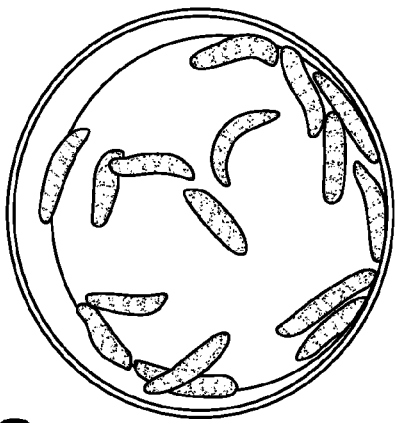
Figure 5C:
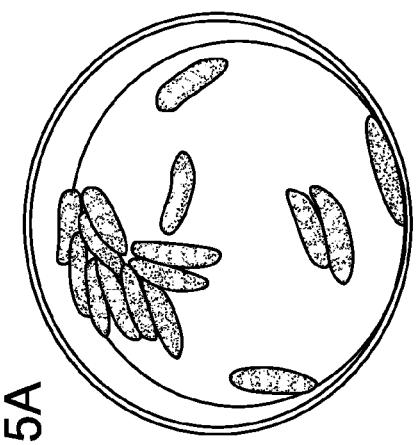
Figure 5D:
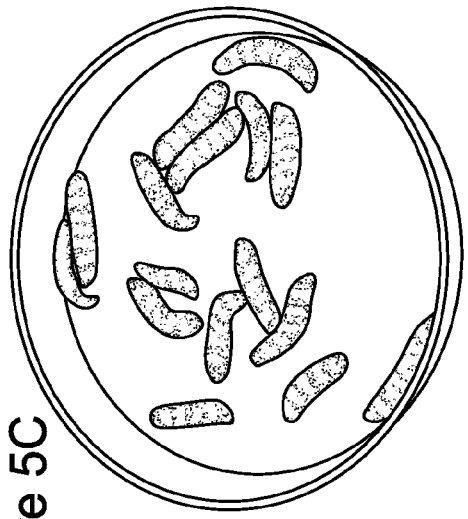
Figure 6A:
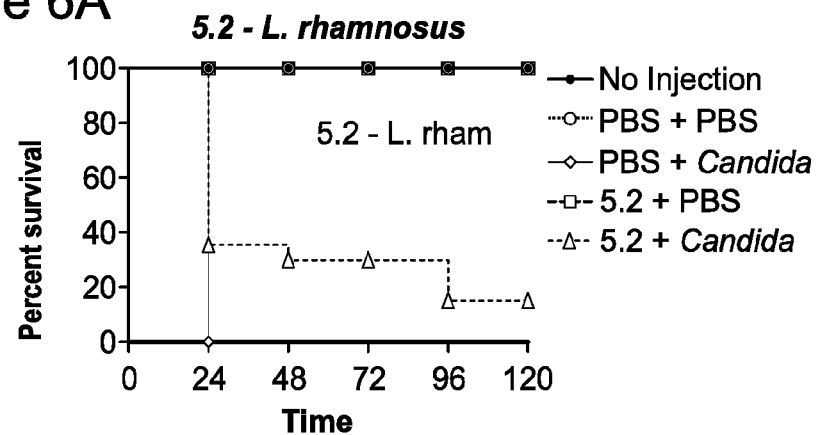
FIG. 6 is a series of line graphs showing *Lactobacillus* spp. prolongs the survival of *G. mellonella* larvae infected with *C. albicans*. There was a significant difference between the "*Lactobacillus* strain+*C. albicans* group" and "PBS+*C. albicans* control group": A. $p=0.0097$; B. $p=0.0013$; C. $p=0.0044$; D. $p=0.0001$; E. $p=0.0245$; F. $p=0.0001$; G. $p=0.0075$; H. $p=0.0003$ and I. $p=0.0733$. Kaplan-Meier test, $p \leq 0.05$.
Figure 6B:
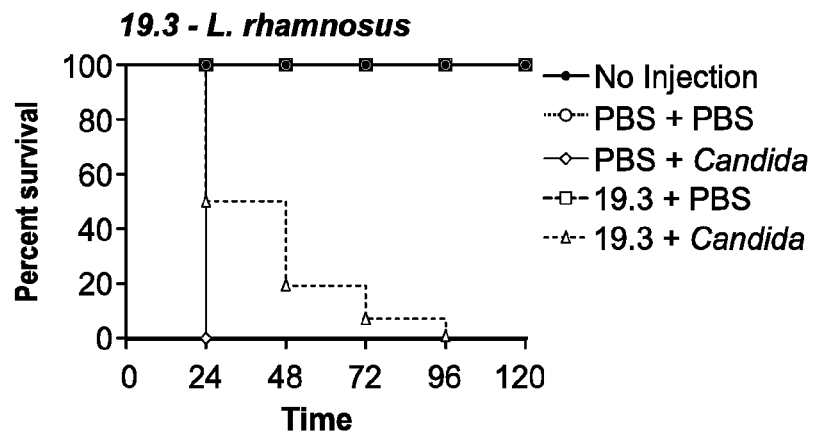
Figure 6C:
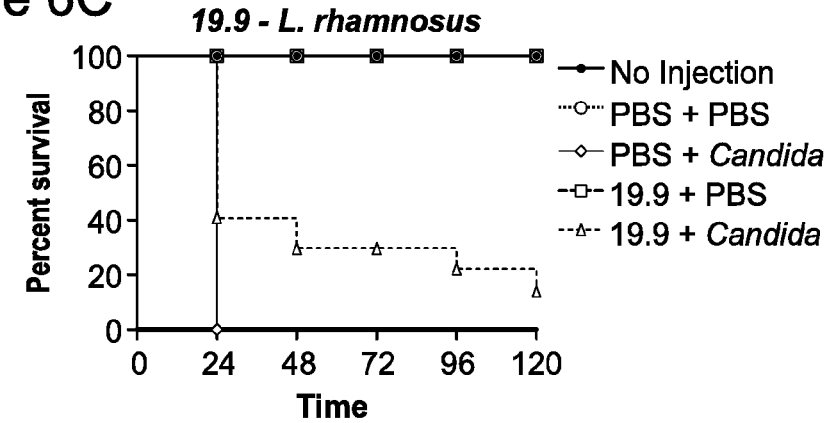
Figure 6D:
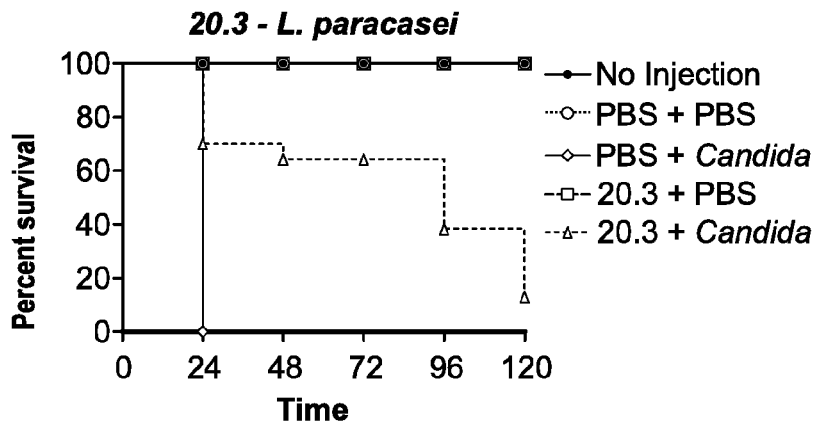
Figure 6E:
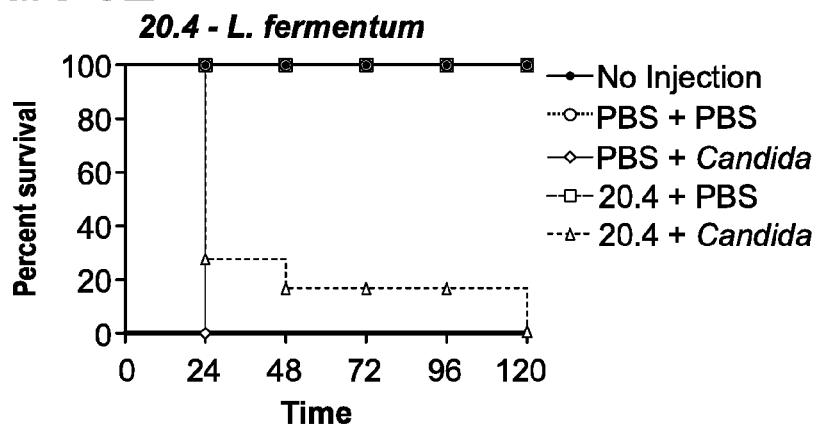
Figure 6F:
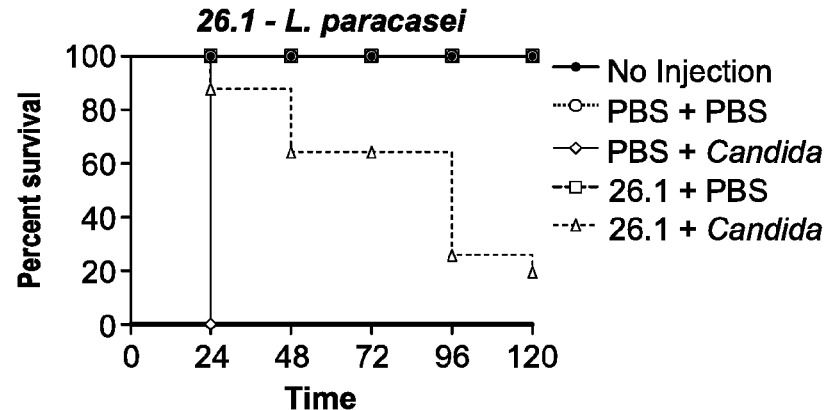
Figure 6G:
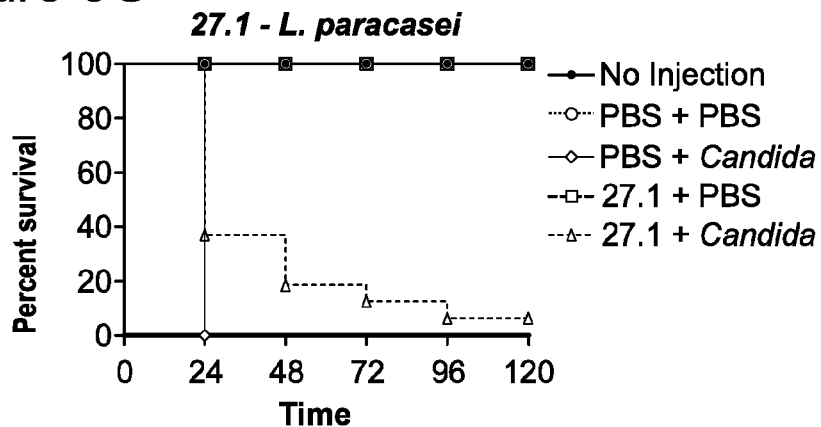
Figure 6H:
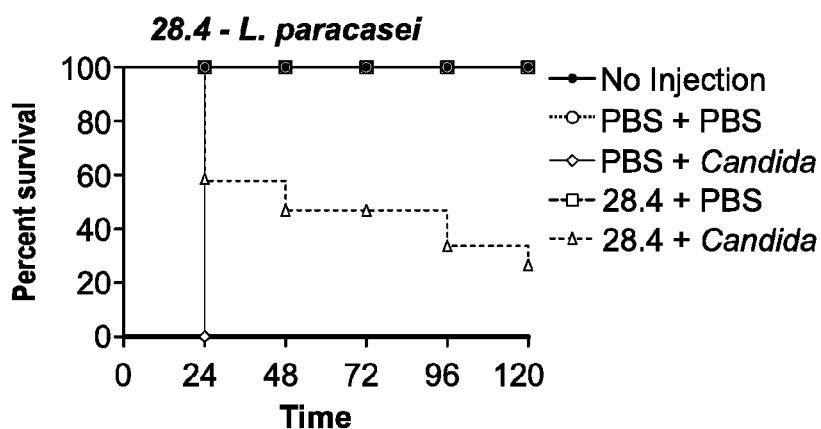
Figure 6I:
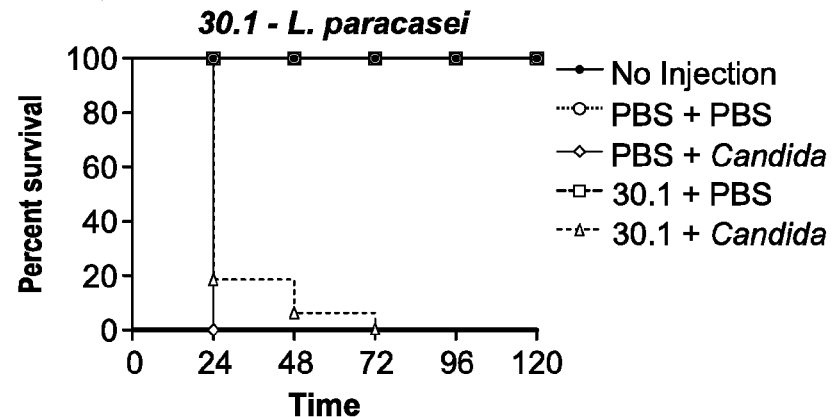
Figure 7:
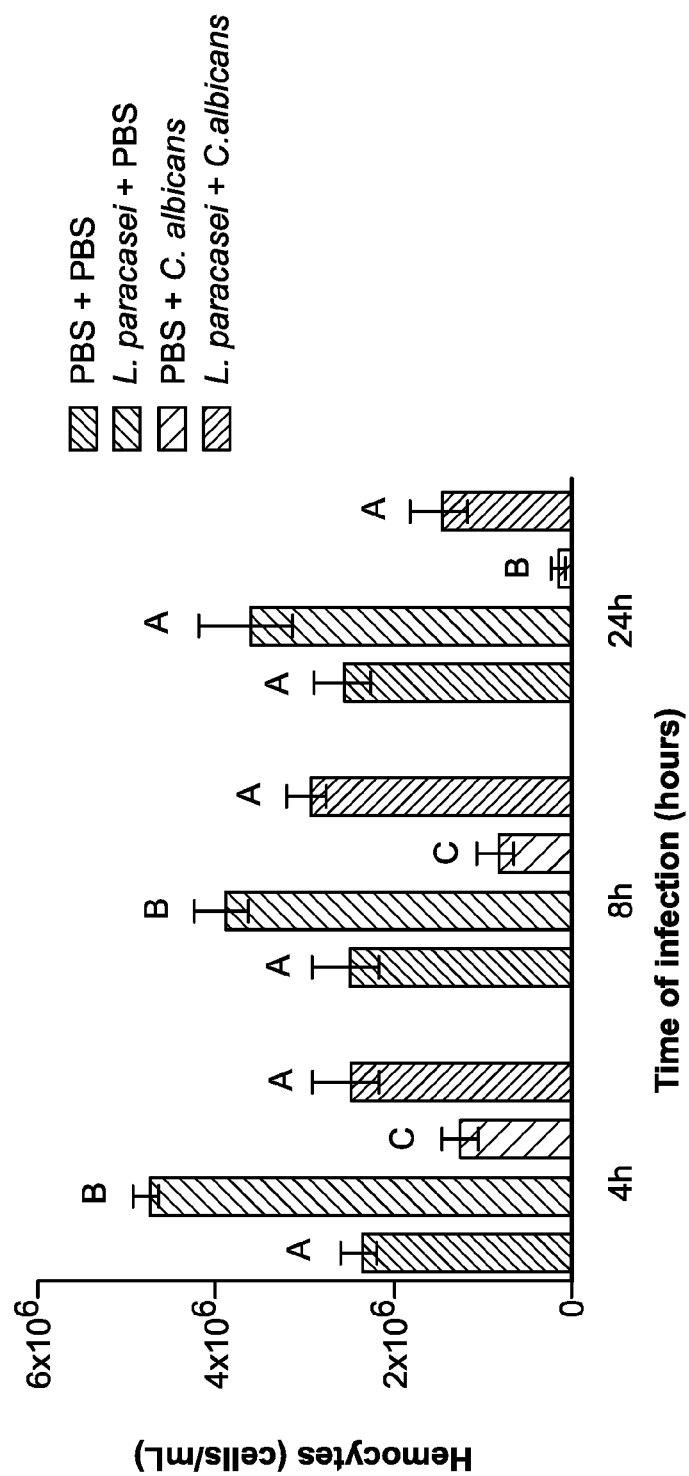
FIG. 7 is a bar graph showing *G. mellonella* hemocyte number increased with the injection of *L. paracasei* strain 28.4. The group of *L. paracasei* 28.4+PBS increased the hemocyte number compared to a PBS control (PBS+PBS) at all different time points studied. The group *L. paracasei*+*C. albicans* also increased the hemocyte quantity compared to *C. albicans* group (PBS+*C. albicans*). PBS+*C. albicans* group showed a reduction of hemocyte quantity in relation to the PBS control group, but when the larvae were pre-treated with *Lactobacillus* (*L. paracasei*+*C. albicans* group) the hemocyte quantity was very similar to the values found in the PBS control group. The four groups were compared in each time point studied by ANOVA test (4 h; $p=0.0001$, 8 h: $p=0.0003$, 24 h: $p=0.0006$). The results of Tukey test are indicated by letters: different letters (A, B, and C) represent statistically significant differences among the groups for each time point studied. A $p \leq 0.05$ value was considered significant.
Figure 8A:
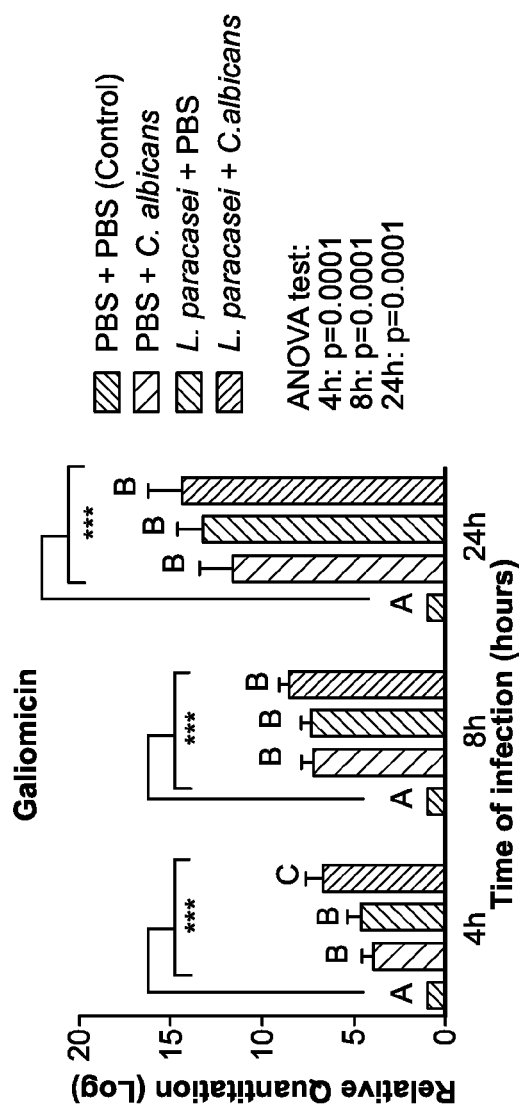
FIG. 8 is a series of bar graphs showing *L. paracasei* strain 28.4 increased the expression of antifungal peptides of *G. mellonella*. Relative quantification (log) of Galiomicin (A) and Gallerymicin (B) for the groups treated with only PBS (Control), pre-treated with PBS and infected with *C. albicans*, only treated with *L. paracasei*, and pre-treated with *L. paracasei* and infected with *C. albicans*. The units in the Y-axis were calculated based on the $2^{-\Delta\Delta CT}$ method, and they are expressed as the means and standard deviation. Each gene was normalized and compared with the expression of insects exposed to the control (PBS) using the reference gene β-actin. Different letters (A, B, and C) represent statistically significant differences among the groups. ANOVA and Tukey Tests ($p \leq 0.05$). ***$p \leq 0.001$.
Figure 8B:
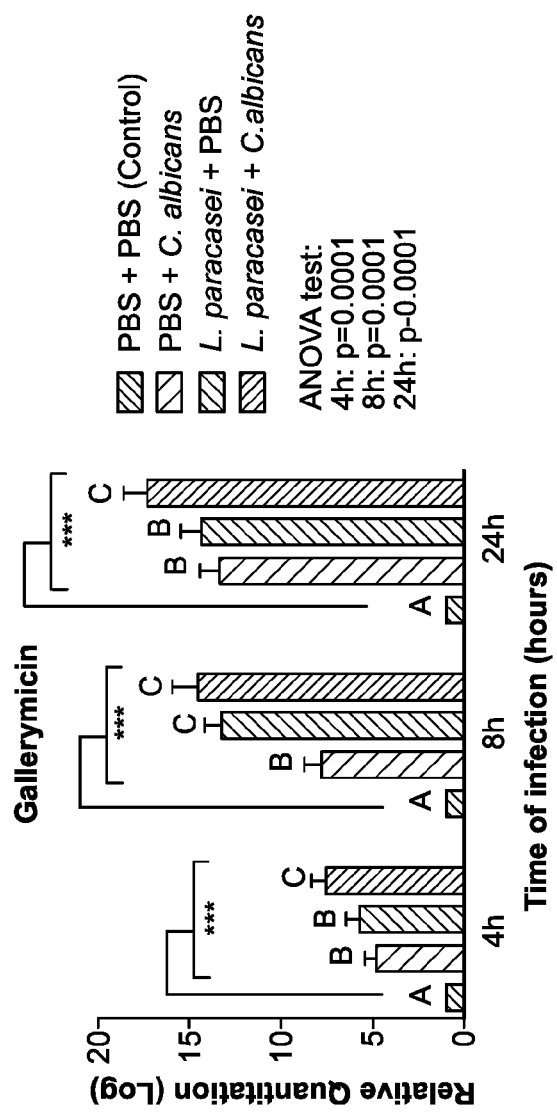
Figure 9:
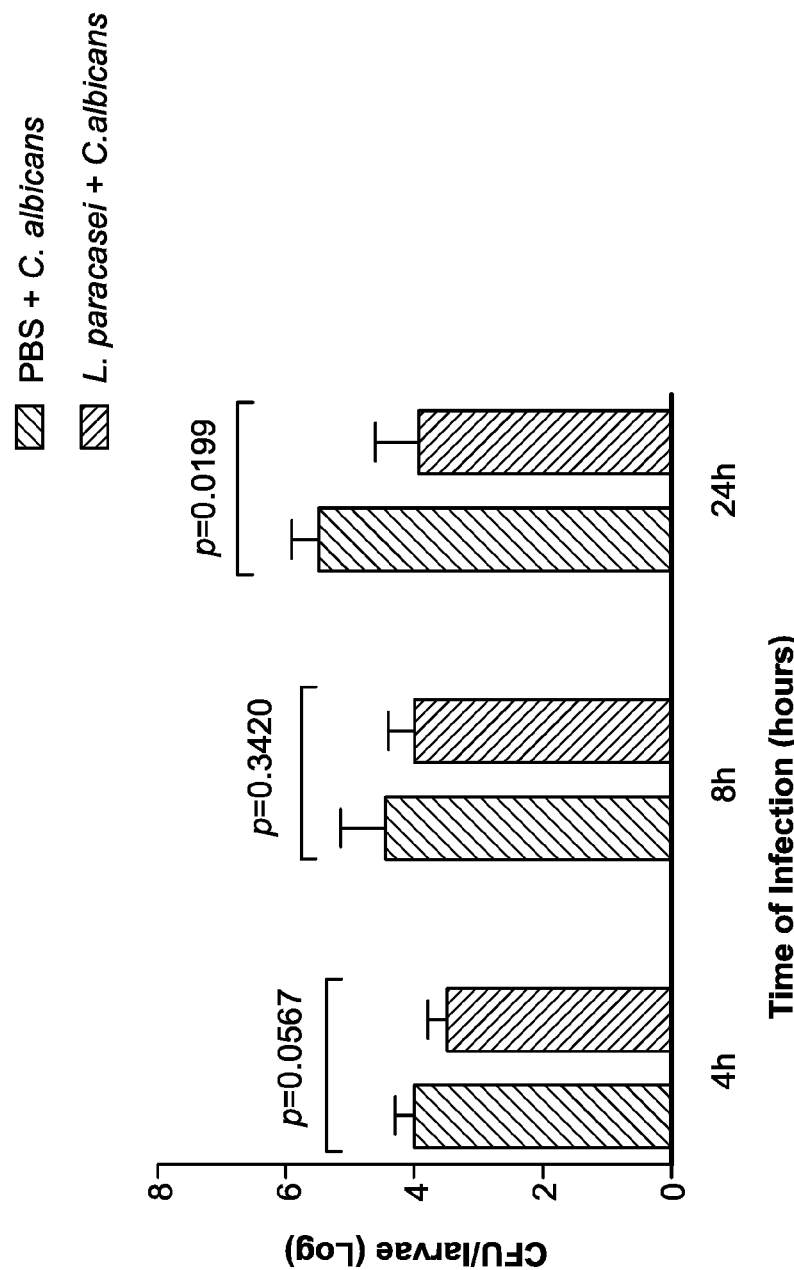
FIG. 9 is a series of bar graphs showing *L. paracasei* strain 28.4 decreased the number of fungal cells in *G. mellonella* hemolymph. Mean and standard deviation of *C. albicans* counts (CFU/larvae) in the hemolymph of *Galleria mellonella* after 4, 8 and 24 h of experimental infection. The following groups were compared at each time of infection: PBS+*C. albicans* (control) and *L. paracasei*+*C. albicans*. A significant difference between groups was only observed after 24 h of infection, with a larger number of CFU/larvae in the control group compared to the *L. paracasei*+*C. albicans* ($p=0.0199$). Student t test, $p \leq 0.05$.

For the gene encoding gallerymicin, the group pretreated with *L. paracasei* and then infected with *C. albicans* had a greater increase in gene expression compared to the other groups for all the times evaluated: 4 h (p=0.0001), 8 h (p=0.0001) and 24 h (p=0.0001). *L. paracasei* increased the expression of the gene encoding gallerymicin according to observation time, achieving 17.29-fold of increase compared to control group formed by PBS+PBS and 1.87-fold compared to control group formed by PBS+*C. albicans* after 24 h (FIG. 4B). These data shows that the pre-treatment with *L. paracasei* strain 28.4 to stimulates the antimicrobial peptide against *C. albicans* in *G. mellonella* model.

Lactobacillus paracasei Probiotic Strains Reduce the Severity of Fungal Infections

*Lactobacilli* spp. are a probiotic bacteria that have excellent health benefits, such as the ability to inhibit the colonization of pathogenic microorganisms, to produce biosurfactants and hydrogen peroxide and to modulate the host immune response (10, 27-29). In this study, we screened new potential probiotic strains of *Lactobacillus* spp. capable to prevent and treat *Candida* infections in *G. mellonella* host model. We also sought to identify immune responses in *G. mellonella* that can be used as substitute markers to predict prophylactic efficacy of a probiotic. We found that *L. paracasei* 28.4 strain improved the survival of *G. mellonella* infected with a lethal inoculum of *C. albicans*. Our results demonstrated that the immune response of *G. mellonella* can be stimulated with a prophylactic provision of probiotic bacteria, making them more resistant to virulent pathogens. These effects were associated with recruitment of hemocytes into the hemolymph and by stimulating antimicrobial peptide response.

Prior to the study of the effects of *lactobacilli* on the development of candidiasis, we evaluated the susceptibility of *G. mellonella* to *Lactobacillus* strains in larvae no infected by *C. albicans*. We observed that the strains did not cause death of the animals in concentrations up to $10^7$ cells/larvae, demonstrating low pathogenicity for *G. mellonella* model. There are few studies that used *G. mellonella* model to the study of probiotics bacteria, in which the strains of *Lactococcus lactis* and *Lactobacillus acidophilus* were not also virulent for this host model (23, 30).

By taking sampling of clinical *Lactobacillus* strains from the oral cavity of healthy patients, we found that some strains provided better protection against *C. albicans* than others. We found that *L. paracasei* 28.4 was the best strain to prevent candidiasis in *G. mellonella* model. Based on these results, we investigated the capacity of this strain to stimulate the immune system of *G. mellonella*. In contrast to the vertebrate animals, the immune system of insects is not composed by immunoglobulin and immune cells with long-term memory. More specifically, the cellular immune response of *G. mellonella* is mediated by hemocytes that represents the main antimicrobial process characterized by phagocytosis (Arvanitis M, Glavis-Bloom J, Mylonakis E. 2013. Biochim Biophys Acta 1832:1378-1383). The humoral immune response involves the production of a various antimicrobial peptides (AMP) that arrest and kill pathogens that evade the cellular immune response (Fallon J P, Troy N, Kavanagh K. 2011. Virulence 2:413-421).

Provision of *L. paracasei* 28.4 strain led an increasing of the survival rate of *G. mellonella* larvae that was accompanied by an increase in the number of hemocytes, demonstrating that *L. paracasei* is capable to stimulate the cellular immune response of the larvae by recruitment of hemocytes. Bergin et al. (Bergin D, Brennan M, Kavanagh K. 2003. Microbes Infect 5:1389-1395) performed a study to evaluate whether fluctuations in the number of hemocytes and yeast cells in infected larvae could be used to determine the relative pathogenicity of a range of strains. The results indicated that larvae inoculated with virulent *Candida* strains showed a significant reduction in density of hemocytes, while the larvae inoculated with strains with low pathogenicity demonstrated only a slight variation in the number of hemocytes. Taken in their totality, these results confirmed that hemocytes could be used to determine the pathogenicity of microorganisms and modulations of the immune response.

The results described herein demonstrate that *Lactobacilli* spp., e.g., *L. paracasei*, lead to broad immunomodulation in the *G. mellonella* model of fungal disease that impacts in the survival of animals during fungal infections.

We also explored alterations in the immune response examining the expression of AMP, including the genes encoding gallerymicin and galiomicin. In *G. mellonella*, the production of AMP represents the last line of defense. These peptides are released into the hemolymph in order to attack elements of the bacterial or fungal cell wall (19, 33). AMP are synthesized as pre-proproteins at a rate up to 100 times faster than IgM in mammals (Lowenberger C. 2001. Insect Biochem Mol Biol 31:219-229) and their small size, less than 10 kDa, allows diffusion through the hemolymph to counteract invading pathogens. In general, the mode of action of AMP is through binding to the surface of pathogens that result in damage to the microbial membrane and lead the collapse of the transmembrane electrochemical gradients (Shai Y. 1999. Biochim Biophys Acta 1462:55-70; Shai Y. 2002. Biopolymers 66:236-248; Brown S E, Howard A, Kasprzak A B, Gordon K H, East P D. 2009. Insect Biochem Mol Biol 39:792-800).

AMP expression in *G. mellonella* treated with probiotic bacteria was found to be modulated such that the immune response against fungal pathogens was augmented. The highest expressions of the genes encoding gallerymicin and galiomicin were found at the times of 8 and 24 h.

The clinical strains of *Lactobacillus* isolated from the oral cavity of healthy patients shows probiotic activity against *C. albicans*. *L. paracasei* 28.4 strain represents a probiotic strain that is useful to control *Candida* infections. In addition, this study indicates that prior exposure to a *L. paracasei* dose activates the *G. mellonella* immune system and allows the larvae to combat a lethal infection by *C. albicans*. This effect is mediated by recruitment of circulating hemocytes, and the production of elevated levels of AMP. This study also demonstrate that *G. mellonella* is a suitable model for analyzing specific aspects of broad probiotic immunomodulation.

The invention claimed is:

1. A composition comprising a purified *Lactobacillus paracasei* bacterium and gellan, wherein said *Lactobacillus paracasei* comprises strain 28.4, and wherein the *Lactobacillus paracasei* strain 28.4 is deposited with ATCC accession number PTA-126984.

2. The composition of claim 1, wherein said composition is in the form of a cream, ointment, or chewing gum.

3. The composition of claim 1, wherein said composition further comprises a human oral cavity-derived *Lactobacillus paracasei*.

4. The composition of claim 2, wherein said composition is in the form of a chewing gum.

5. The composition of claim 1, wherein said composition is in the form of a chewable tablet.

6. A chewing gum composition comprising a *Candida albicans*-inhibiting purified *Lactobacillus paracasei* bacterium and a gellan, wherein said *Candida albicans*-inhibiting purified *Lactobacillus paracasei* comprises *Lactobacillus paracasei* strain 28.4, deposited with ATCC accession number PTA-126984.

\* \* \* \* \*